(12) United States Patent
Miller et al.

(10) Patent No.: US 6,743,182 B2
(45) Date of Patent: Jun. 1, 2004

(54) METHOD FOR DETERMINING ATTENTION DEFICIT HYPERACTIVITY DISORDER (ADHD) MEDICATION DOSAGE AND FOR MONITORING THE EFFECTS OF (ADHD) MEDICATION

(75) Inventors: Paige Miller, Rochester, NY (US); David L. Patton, Webster, NY (US); Richard N. Blazey, Penfield, NY (US)

(73) Assignee: The McLean Hospital Corporation, Belmont, MA (US)

( * ) Notice: Subject to any disclaimer, the term of this patent is extended or adjusted under 35 U.S.C. 154(b) by 6 days.

(21) Appl. No.: 10/301,401

(22) Filed: Nov. 21, 2002

(65) Prior Publication Data

US 2003/0100844 A1 May 29, 2003

Related U.S. Application Data

(63) Continuation-in-part of application No. 09/865,329, filed on May 25, 2001, now Pat. No. 6,520,921.

(51) Int. Cl.$^7$ .................................................. A61B 5/00
(52) U.S. Cl. ........................................ 600/549; 600/300
(58) Field of Search .............................. 600/300, 301, 600/509, 536, 544, 549, 545, 558, 546, 26–28, 483, 484; 128/898, 897, 905, 920; 434/236, 238

(56) References Cited

U.S. PATENT DOCUMENTS

| | | |
|---|---|---|
| 5,377,100 A | 12/1994 | Pope et al. |
| 5,913,310 A | 6/1999 | Brown |
| 5,918,603 A | 7/1999 | Brown |
| 5,940,801 A | 8/1999 | Brown |
| 6,053,739 A | 4/2000 | Stewart et al. |
| 6,097,980 A | 8/2000 | Monastra et al. |
| 6,117,075 A | 9/2000 | Barnea |
| 6,482,165 B1 * | 11/2002 | Patton et al. ............... 600/549 |
| 6,652,470 B2 * | 11/2003 | Patton et al. ............... 600/549 |

OTHER PUBLICATIONS

Nature Medicine, vol. 6, No. 4, Apr. 2000, pp 470–473.
Lubar, Biofeedback and Self–Regulation, vol. 16, No. 3, 1991, pp 201–225.
V. Shusterman, O. Barnea, Biofeedback and Self–Regulation, vol. 20, No. 4, 1995.
K.B. Raymond, Dissertation Abstracts International, Section A: Humanities and Social Services, 57 (12–A) 5052, 1997.
L. Katz, G. Goldstein, M. Geckle, Journal of Attention Disorders, 2 (4), 239–47, 1998.

* cited by examiner

*Primary Examiner*—Tu Ba Hoang
(74) *Attorney, Agent, or Firm*—Clark & Elbing LLP (57) ABSTRACT

A method for determining the appropriate dosage of a medication to treat Attention Deficit Hyperactivity Disorder (ADHD) in an individual who has ADHD comprising: sampling the peripheral skin temperature of a human subject during a predetermined time interval when the subject is in an inactive state to provide sampled peripheral skin temperature data; analyzing the sampled peripheral skin temperature data for a pre-selected parameter to determine whether the pre-selected parameter has a value indicative of ADHD; and determining the proper dosage of a medication to treat ADHD based upon the determined value of the pre-selected parameter. At a time subsequent to administering the dosage, it is determined if a previously administered dosage of a medication is effective at removing the effects of ADHD as measured by this pre-selected parameter.

19 Claims, 9 Drawing Sheets

METHOD FOR DETERMINING ATTENTION DEFICIT HYPERACTIVITY DISORDER (ADHD) MEDICATION DOSAGE AND FOR MONITORING THE EFFECTS OF (ADHD) MEDICATION

CROSS REFERENCE TO RELATED APPLICATIONS

This patent application is a Continuation-in-Part Application of U.S. patent application Ser. No. 09/865,329 filed May 25, 2001, now U.S. Pat. No. 6,520,921 which application claims the benefit under 35 USC §120 of the earlier filing date of U.S. patent application Ser. No. 09/597,610, filed Jun. 20, 2000, now U.S. Pat. No. 6,394,963.

FIELD OF THE INVENTION

This invention relates in general to a technique for monitoring the effectiveness of medication taken to treat Attention Deficit Hyperactivity Disorder (ADHD) and more particularly to a technique for measuring an individual's peripheral temperature variability (TV) indicative of ADHD.

BACKGROUND OF THE INVENTION

ADHD is the most common neurobehavioral disorder of childhood as well as among the most prevalent health conditions affecting school-aged children. Between 4% and 12% of school age children (several millions) are affected. $3 billion is spent annually on behalf of students with ADHD. Moreover, in the general population, 9.2% of males and 2.9% of females are found to have behavior consistent with ADHD. Upwards of 10 million adults may be affected.

ADHD is a difficult disorder to diagnose. The core symptoms of ADHD in children include inattention, hyperactivity, and impulsivity. ADHD children may experience significant functional problems, such as school difficulties, academic underachievement, poor relationships with family and peers, and low self-esteem. Adults with ADHD often have a history of losing jobs, impulsive actions, substance abuse, and broken marriages. ADHD often goes undiagnosed if not caught at an early age and affects many adults who may not be aware of the condition. ADHD has many look-alike causes (family situations, motivations) and co-morbid conditions (depression, anxiety, and learning disabilities) are common.

Diagnosis of ADHD involves a process of elimination using written and verbal assessment instruments. However, there is no one objective, independently validated test for ADHD. Various objective techniques have been proposed but have not yet attained widespread acceptance. These include:

1. The eye problem called convergence insufficiency was found to be three times more common in children with ADHD than in other children by University of California, San Diego researchers.
2. Infrared tracking to measure difficult-to-detect movements of children during attention tests combined with functional MRI imaging of the brain were used by psychiatrists at McLean Hospital in Belmont, Mass. to diagnose ADHD in a small group of children (*Nature Medicine*, Vol. 6, No. 4, April 2000, Pages 470–473).
3. Techniques based on EEG biofeedback for the diagnoses and treatment of ADHD are described by Lubar (*Biofeedback and Self-Regulation*, Vol. 16, No. 3, 1991, Pages 201–225).
4. U.S. Pat. No. 6,097,980, issued Aug. 1, 2000, inventor Monastra et al, discloses a quantitative electroencephalographic process assessing ADHD.
5. U.S. Pat. No. 5,913,310, issued Jun. 22, 1999, inventor Brown, discloses a video game for the diagnosis and treatment of ADHD.
6. U.S. Pat. No. 5,918,603, issued Jul. 6, 1999, inventor Brown, discloses a video game for the diagnosis and treatment of ADHD.
7. U.S. Pat. No. 5,940,801, issued Aug. 17, 1999, inventor Brown, discloses a microprocessor such as a video game for the diagnosis and treatment of ADHD.
8. U.S. Pat. No. 5,377,100, issued Dec. 27, 1994, inventors Pope et al., discloses a method of using a video game coupled with brain wave detection to treat patients with ADHD.
9. Dr. Albert Rizzo of the Integrated Media Systems Center of the University of Southern California has used Virtual Reality techniques for the detection and treatment of ADHD.
10. U.S. Pat. No. 6,053,739, inventors Stewart et al., discloses a method of using a visual display, colored visual word targets and colored visual response targets to administer an attention performance test. U.S. Pat. No. 5,377,100, issued Dec. 27, 1994, inventors Patton et al., discloses a system and of managing the psychological state of an individual using images. U.S. Pat. No. 6,117,075 Barnea discloses a method of measuring the depth of anesthesia by detecting the suppression of peripheral temperature variability.

There are several clinical biofeedback and physiologic monitoring systems (e.g. Multi Trace, Bio Integrator). These systems are used by professional clinicians. Although skin temperature spectral characteristics have been shown to indicate stress-related changes of peripheral vasomotor activity in normal subjects, there has been no disclosure of use of variations in skin-temperature response to assist in diagnosing ADHD. (See: Biofeedback and Self-Regulation, Vol. 20, No. 4, 1995).

As discussed above, the primary method for diagnosing ADHD is the use of a bank of written and verbal assessment instruments designed to assess the children for behavioral indicators of criteria established by American Medical Association (AMA) as described in the Diagnostic and Statistics manual-IV (DSM-IV). Psychiatrists, psychologists, school psychologists and other licensed practitioner administer these assessment instruments. In some cases those individuals who meet DSM-IV criteria for ADHD diagnosis are prescribed a drug such as Ritalin. Behavioral observations of the patient while on Ritalin are conducted to assess the impact of prescribed medication. However, clearly established criteria for evaluating the impact of specific medications e.g., Ritalin and specific dosages are lacking. It would be advantageous for physicians to have access to clearly established physiologic criteria, which could be measured, to determine if a specific medication at a specific dosage effectively addressed the underlying physiologic parameter, which was indicative of ADHD.

There is thus a need for a simple, inexpensive, and reliable technique for determining the effectiveness of the medication and appropriate dosage taken to counteract ADHD by an individual who has ADHD.

SUMMARY OF THE INVENTION

According to the present invention, there is provided a solution to the problems and fulfillment of the needs discussed above.

According to a feature of the present invention, there is provided a a method for determining the appropriate dosage of a medication to treat Attention Deficit Hyperactivity Disorder (ADHD) in an individual who has ADHD comprising:

measuring the stress of a human subject by sampling the peripheral skin temperature of a human subject during a predetermined time interval when the subject is in an inactive state to provide sampled peripheral skin temperature data;

analyzing the sampled peripheral skin temperature data for a pre-selected parameter to determine whether said pre-selected parameter has a value indicative of ADHD; and determining the proper dosage of a medication to treat ADHD based upon said determined value of said pre-selected parameter; and at a time subsequent to administering said dosage, determining if the administered dosage of medication is actually effective at removing the effects of ADHD as measured by said pre-selected parameter.

ADVANTAGEOUS EFFECT OF THE INVENTION

The invention has the following advantages.

1. A device and technique for determining the effectiveness of the medication and appropriate dosage taken to counteract ADHD by an individual whom has ADHD which is simple, inexpensive and reliable.

DETAILED DESCRIPTION OF THE INVENTION

According to the invention, it has been found that a signature of ADHD is hidden in fluctuation of the temperature of the skin as measured at the extremities such as at a fingertip as a function of variations in stress level. In general, as an individual's stress level increases the peripheral vasculature constricts and often the person's blood pressure increases. As the blood vessels in the body constrict, blood flow is restricted. This is most easily monitored in the extremities such as the fingers, because the blood vessels in the extremities are small and very responsive to Sympathetic Nervous System (SNS) innervations. A direct result of decreased blood flow to the blood vessels in the extremities is a decrease in the peripheral temperature of the extremities. Conversely, as an individual's stress level decreases and relaxation occurs, the blood vessels expand, allowing blood to flow in a less restricted manner. As the blood flow to the vessels in the extremities increases the peripheral temperature of the extremities increases. It is suspected that when a subject with ADHD is subjected to sensory deprivation such as being made to look at a blank screen or an obscured image for a period of time in an inactive state, the lack of stimulation increases and there tends to be a shift in the subject's physiologic reactivity indicative of an increase in their stress level. As their stress level increases their blood vessels contract and the peripheral temperature of their extremities decreases. Biofeedback practitioners have long used measurement of hand temperature to help subjects manage their physiology by controlling blood flow to the extremities. The literature reports that reduced blood flow to the brain is frequently found in patients with ADHD.

In addition to peripheral skin temperature and peripheral skin temperature variability there are other known physiologic measures which are known (or potential) indicators of stress and therefore ADHD such as; bilateral temperature variability, heart rate, heart rate variability, muscle tension (excessive and chronic, measured via surface electromyography—sEMG), bilateral muscle tension imbalance, galvanic skin response (i.e., electro dermal response—EDR), eye saccades, blood oxygen ($SpO_2$), salivary IGA, electroencephalography (EEG), peripheral blood flow (measured via photoplethismography—PPG), and peripheral blood flow variability (PPG).

Figure 1:
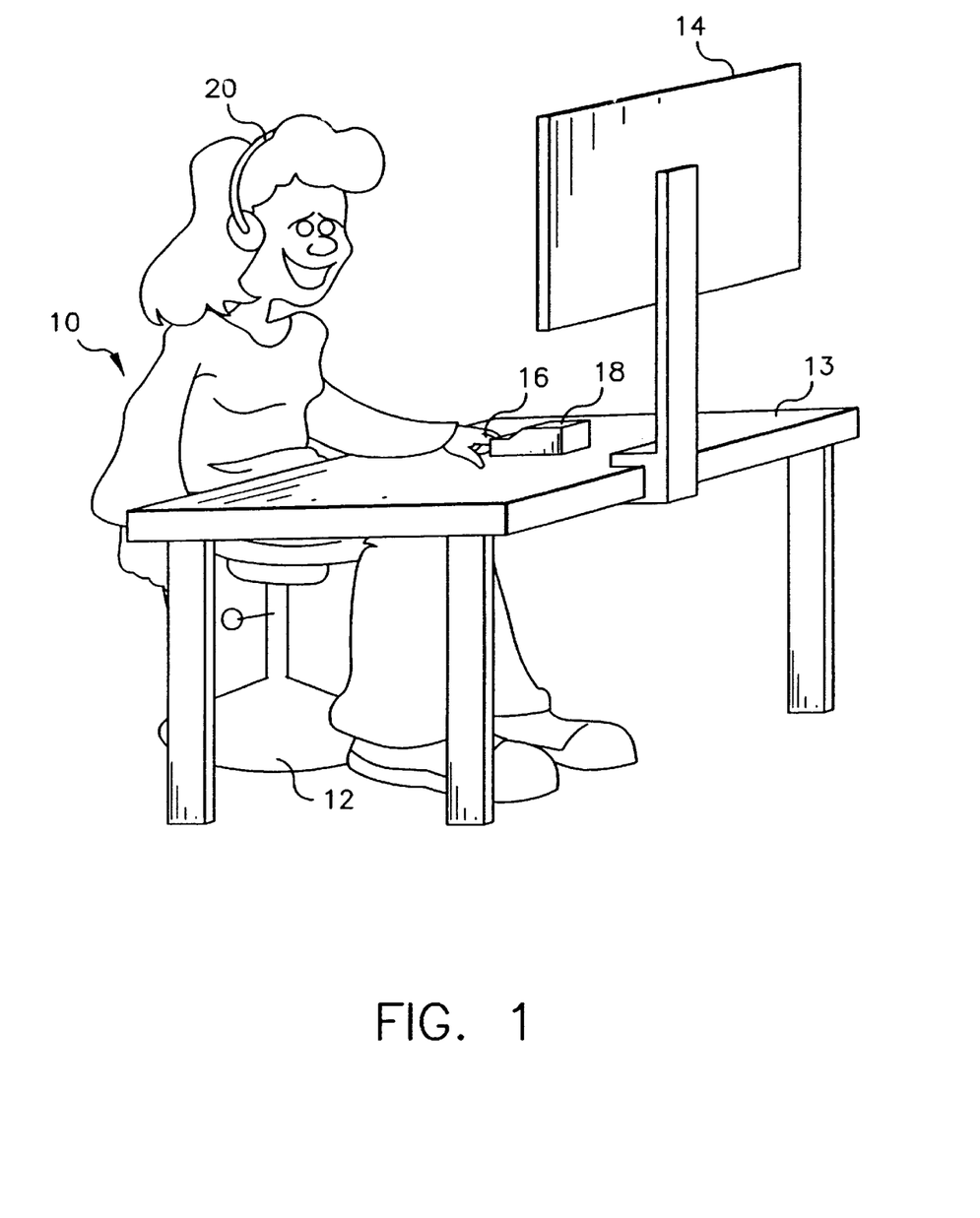
FIG. 1 is a diagrammatic view illustrating use of an embodiment of the present invention.

As shown in FIG. 1, a subject 10 is sitting on a chair 12 at a table 13 watching a screen 14. The screen 14 is used to block any visual stimulus from disturbing the subject 10. The subject 10 is wearing a set of earphones 20. The earphones 20 can be connected to a sound-generating device not shown. The earphones 20 can be used to block out ambient noise or to produce a white noise intended to reduce or eliminate the audio stimulus from the environment during the test. The subject is at rest in an inactive state. During the test no visual or auditory stimulus is provided to the subject. The fingertip 16 of subject 10 is inserted into an analyzer module 18, where the skin temperature is measured via a sensor 22 (shown in FIG. 2). In another embodiment of the present invention, which is not shown, the subject can wear a pair of translucent glasses, goggles or eye mask. The glasses or goggles are used to block any visual stimulus from the subject.

Figure 2:
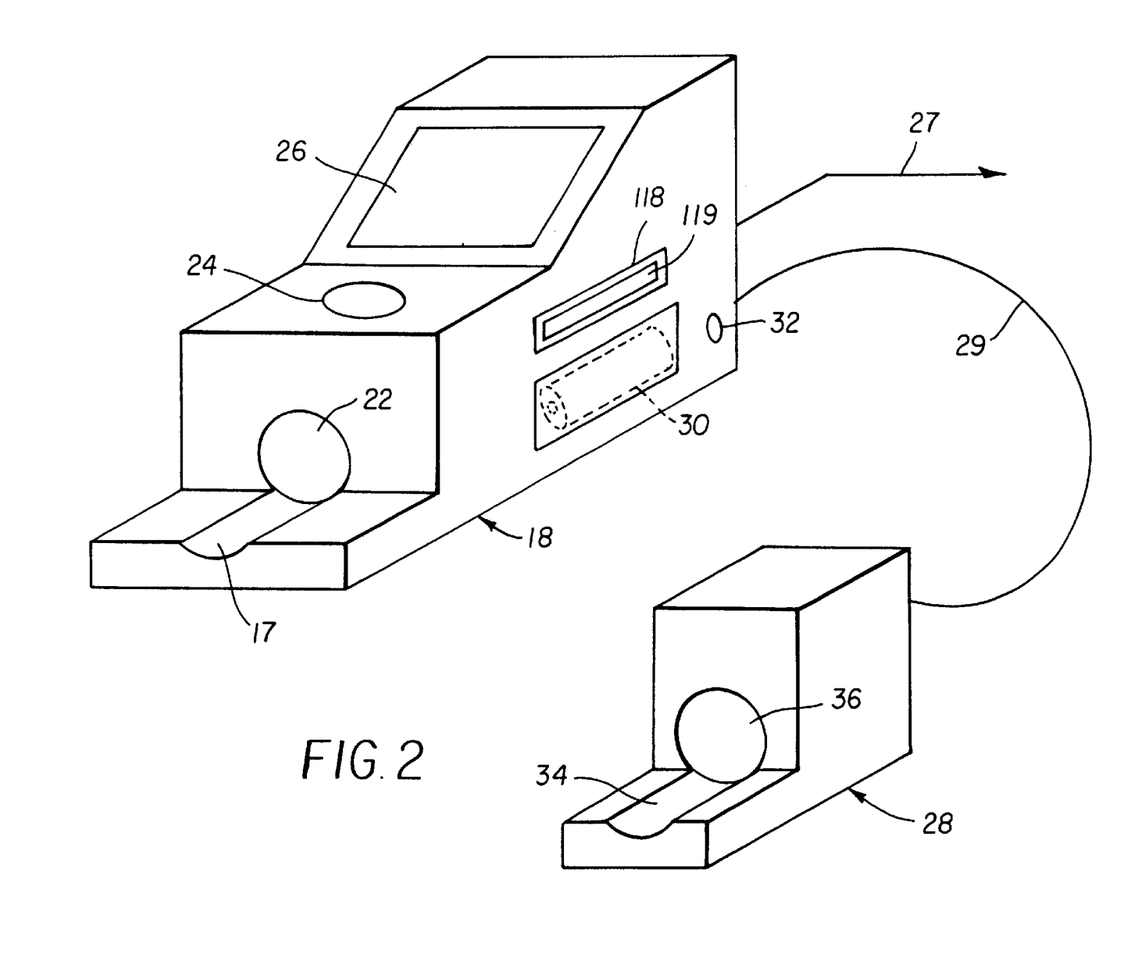
FIG. 2 is a perspective view showing in greater detail the embodiment of FIG. 1.

FIG. 2 shows an illustration of the analyzer module 18. Analyzer module 18 includes a temperature sensor 22, where the subject 10 inserts their fingertip 16 in groove 17, an on/off switch 24, and a display 26. The analyzer module 18 can have an internal power supply, such as a battery 30, or an external low voltage power supply port 32 for an external low voltage power supply (not shown), such as used for a telephone. The analyzer module 18 can be connected to an external CPU (not shown) via a cable 27 (such as an USB or RS 232 cable), or wireless transmitting device such as an RF or IR link (not shown). In a further embodiment a second temperature sensor module 28 can be connected to the analyzer 18 via a cable 29. The second temperature sensor module 28 can be used to sample the skin temperature of the subject's 10 other hand and includes groove 34 and temperature sensor 36.

Figure 3A:
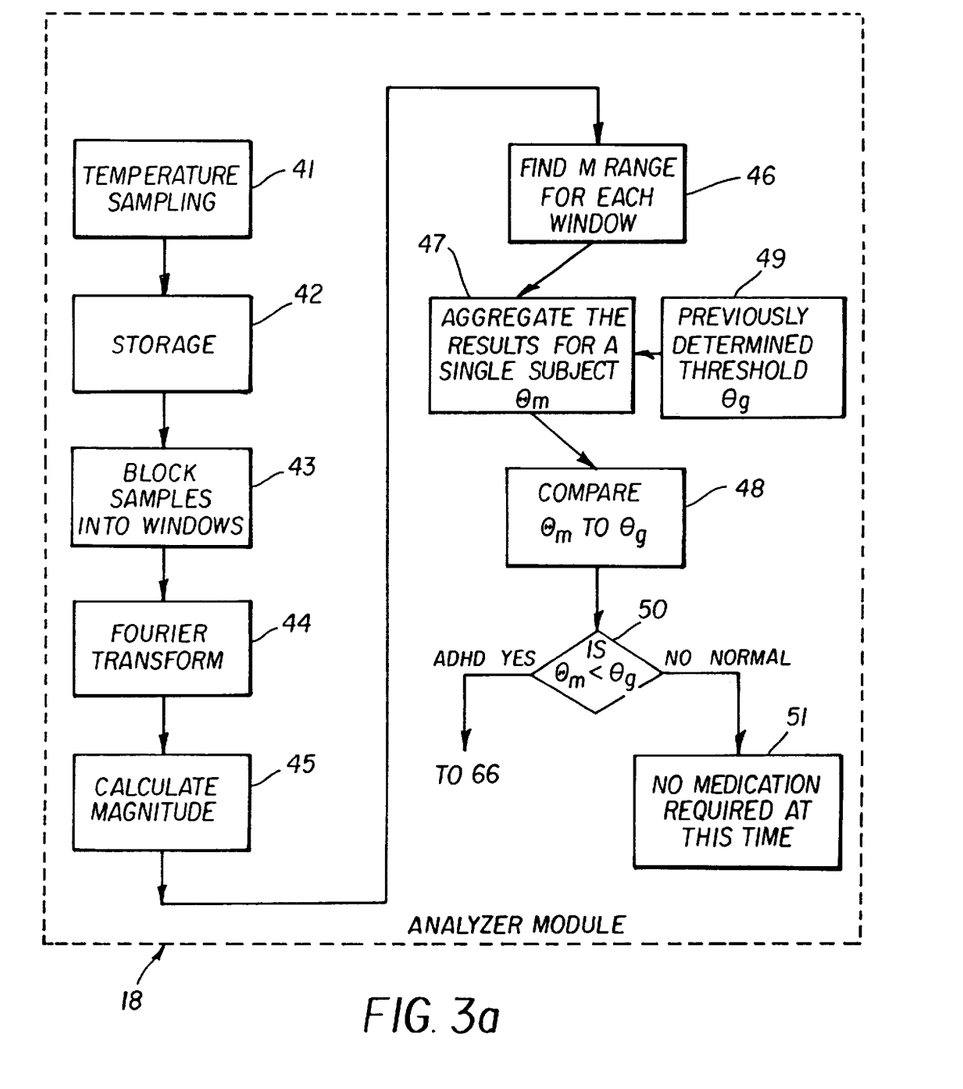
FIGS. 3a and 3b are block diagrams of a system incorporating the present invention.

As shown in FIG. 3a, module 18 includes temperature sampling circuit 41, data storage 42, window blocking 43, Fourier transform 44, Magnitude calculation 45, Mrange calculation 46, aggregation step block 47, Threshold comparison step block 48, previously determined threshold $\theta_g$ block 49, and threshold comparison decision block 50. The method of determining dosage is further expanded in FIG. 3b.

In FIG. 1, the fingertip temperature is first recorded during an interval when the subject 10 has been asked to sit quietly for a period of about 10 minutes. The temperature data is sampled by 41 at a time interval $\Delta t$ creating a list of n temperature samples, which are stored in storage 42.

Now referring to FIG. 3$a$, in block 43, the n samples are divided into z windows of m samples, each group corresponding to a given time window of width $\Delta t$ (~32–64 sec) equally spaced in time (~50 sec) across the entire data collection time interval $\Delta t$. The data from each window is then passed through a Fast Fourier Transform (FFT) algorithm 44 producing $2^{m-1}$ data points spaced equally in frequency space for each window. The values are complex numbers having form $$FFT(f_m) = A(f_m) + B(f_m)i$$

where i is the $\sqrt{-1}$. The Phase $\Phi(f_m)$ is then found from the equation $$\Phi_l(f_m) = \operatorname{Tan}^{-1}\left(\frac{B(f_m)}{A(f_m)}\right) \quad (1.0)$$

and the Magnitude $M(f_m)$ from $$M_l(f_m) = \sqrt{B(f_m)^2 + A(f_m)^2} \quad (1.1)$$

Figure 4:
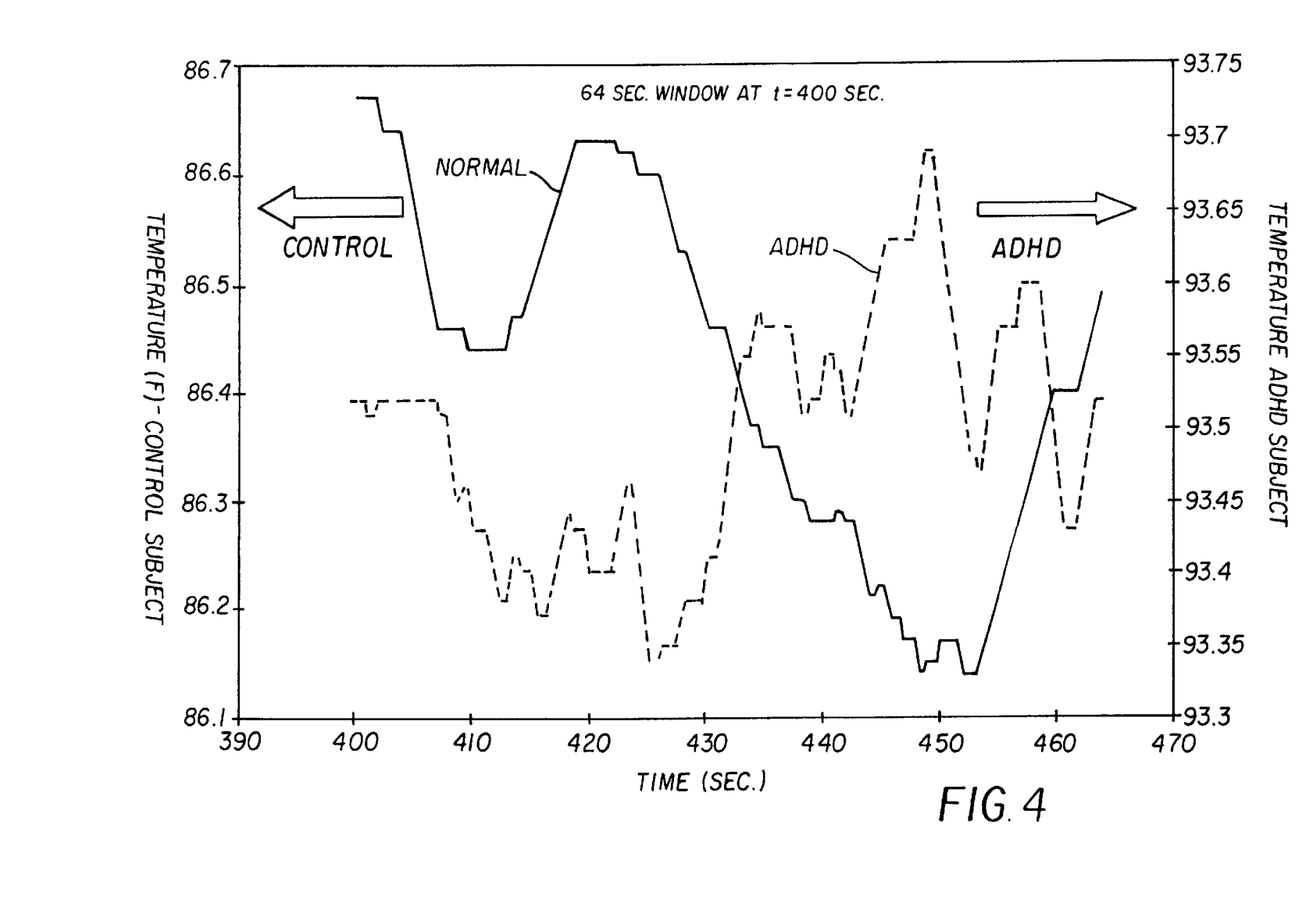
FIGS. 4, 5 and 6 are graphical views useful in explaining the present invention.

In the equations 1.0 and 1.1 the subscript l refers to the fact that a separate signal is extracted for each hand so the subscript is l for data extracted from the left-hand data and r for data from the right hand. FIG. 4 graphically illustrates the temperature signal during one window for a normal subject and a person diagnosed with ADHD.

Figure 5:
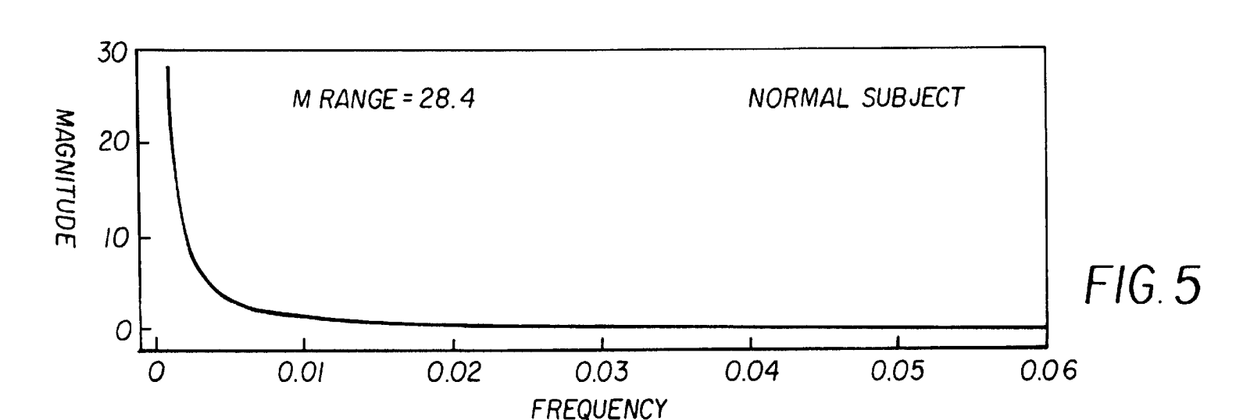
Figure 6:
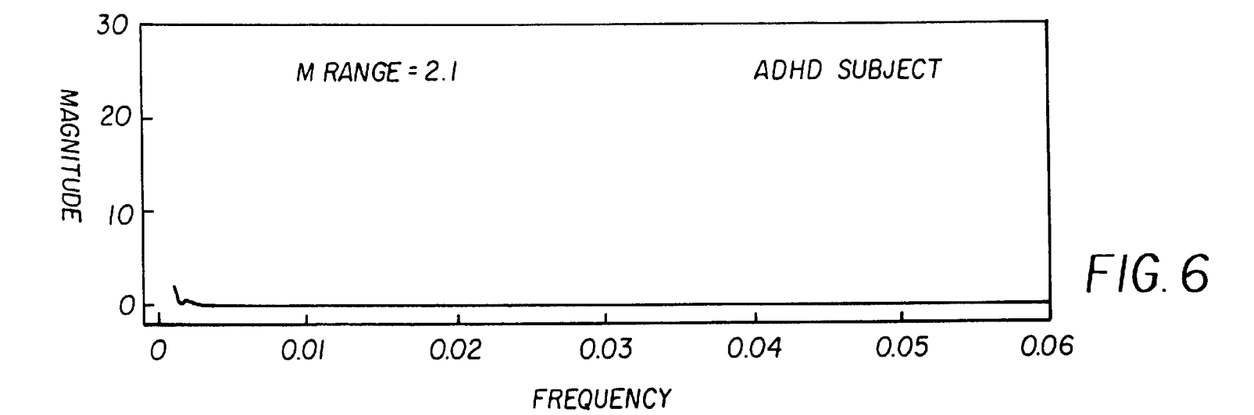
Figure 7:
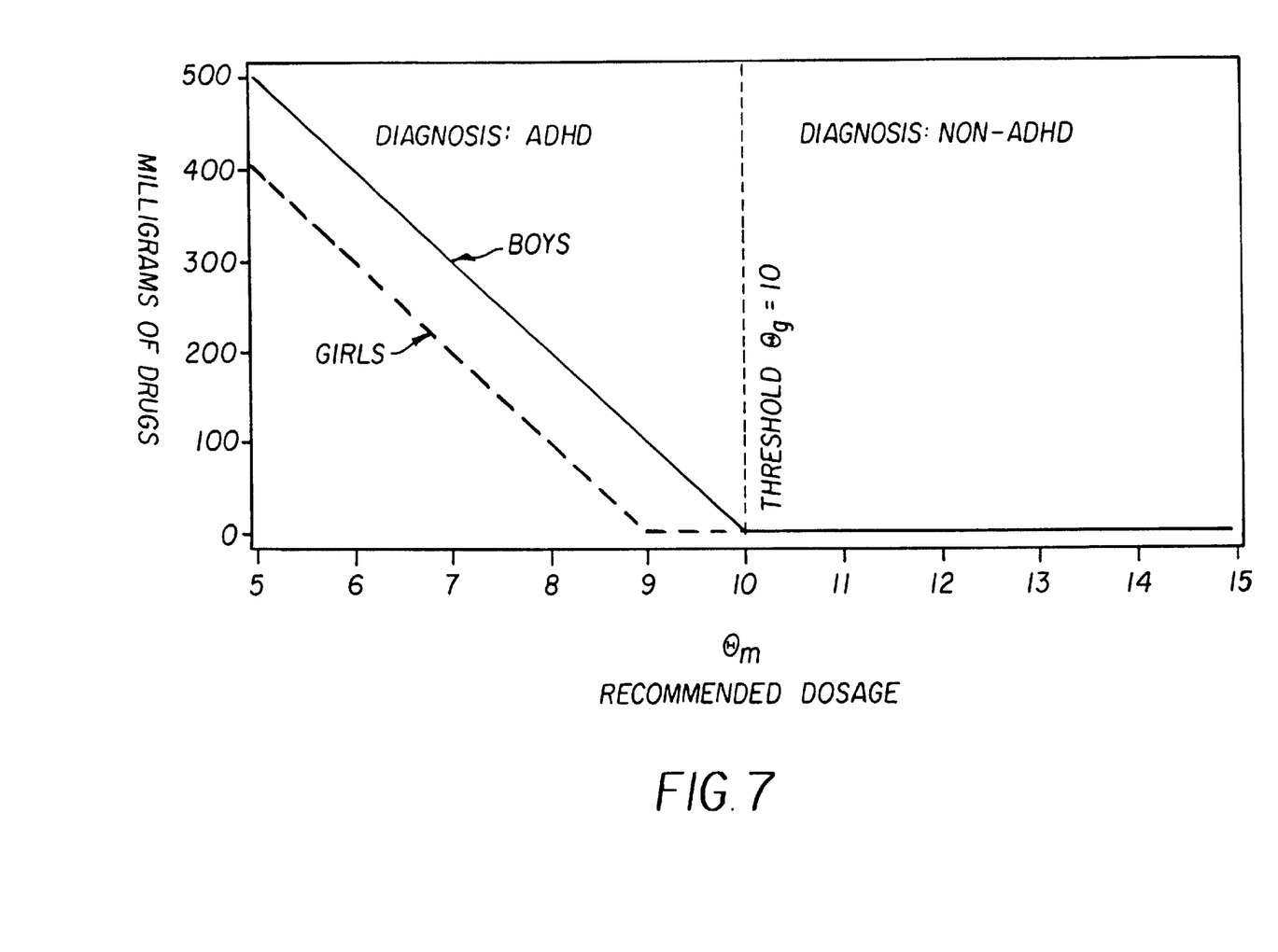
FIG. 7 is a diagram of an example of using the threshold $\theta_g$ and the patient's computed aggregation statistic $\Theta_m$ to diagnose the presence or absence of ADHD and determine the suggested drug dosage.

FIGS. 5 and 6 graphically illustrate the magnitude transform for the data corresponding with a subject with ADHD and normal subject. In FIG. 5, the magnitude spectrum undergoes dramatic changes essentially changing from a hyperbolic curve to a flat response for a normal subject. In FIG. 6, the magnitude range is substantially less than shown in FIG. 5, indicating ADHD.

Raw Data

The raw data $T_{k,l}(t)$ is the temperature taken from hand l at a fingertip 16 as shown in FIG. 1, during the 10-minute session. The sessions were taken over a period of weeks. Some subjects had as few as 2 sessions and some as many as 5 sessions. k is used to represent the session.

Referring again to FIG. 3$a$:

Windows

The data for each session were divided into a series of windows (block 43) prior to performing the Fourier Transform operation. Call the window width w. In this analysis, the window width was 64 seconds and there were 10 windows spaced at 50-second intervals (the windows overlap) across the 600 sec baseline spanning the range of 100–500 sec, other values of w can be used. The window number in a session is referred to with the letter j. For each window a FFT algorithm calculates the Fourier Transform F(f). The Magnitude and Phase of this transform are defined as given above.

In block 46 the range of magnitude variation during a window is calculated using equation (1.2) below where $f_{max}$ and $f_{min}$ are the frequencies where the Magnitude is the greatest and the least respectively (note the dc component at frequency zero is excluded).

$$M_{range} = [M(f_{max}) - M(f_{min})] \quad (1.2)$$

In a further embodiment of this method, other statistics from a Fourier Transform, calculated from the quantities denoted above as $A(f_m)$, $B(f_m)$, $\theta(f_m)$, and $M(f_m)$ may be used. In addition to using Fourier Transforms, this further embodiment may use statistics derived from a Wavelet transform of data or other filtering of the data (as in Strang, G. and Nguyen, T. (1996), *Wavelets and Filter Banks*, Wellesley-Cambridge Press, Wellesley, Mass.).

Aggregation of Samples

MRange values for all windows are aggregated in block 47. There are z windows from each hand from each session. The first step is to choose an aggregation statistic, which can be the mean, median, variance, or other statistic, which is an aggregate of the computed $M_{range}$ values in each window for each session and each hand. Other statistics that may be used for aggregation include the standard deviation, range, interquartile distance, skewness, kurtosis, Winsorized mean and variance, and robust estimates of mean and variance. Equations below are given for aggregating the mean and the variance. The mean magnitude range for the left hand during session k is found from equation 2.0. where z is the number of windows in the session.

$$<M_{k,l}> = \frac{\sum_{j=1}^{z}[M(f_{max})_j - M(f_{min})_j]}{z} \quad (2.0)$$

And the corresponding variance is:

$$<Var_{k,l}> = \frac{\sum_{j=1}^{z}\{[M(f_{max})_{j,l} - M(f_{min})_{j,l}] - <M_{k,l}>\}^2}{z-1} \quad (2.1)$$

Combining these session means and variances over both hands and all the sessions s that a subject attended gives an aggregated mean $\mu$ and aggregated variance.

$$\mu = \frac{\sum_{k=1}^{s}\sum_{l=1}^{2}<M_{k,l}>}{2s} \quad (2.2)$$

$$<var> = \frac{\sum_{k=1}^{s}\sum_{l=1}^{2}var_{k,l}}{2s} \quad (2.3)$$

Further embodiments of this aggregation step include using the data from only one hand—either the left hand, the right hand, or the dominant hand (and if the subject is ambidextrous, the dominant hand would be defined as the average of both hands). In addition, future embodiments may not require averaging of several sessions, but selecting only one session for use or using a weighted combination of each session's results.

Diagnostic Indicators

Referring again to FIG. 3$a$, the normalized group diagnostic threshold indicator $\theta_g$ was established previously from the aggregation statistics determined using data from a large group of subjects having similar demographic characteristics-block 49, and can vary based upon gender, age or weight. This group diagnostic threshold $\theta_g$ is calculated statistically from group temperature variability data using methods described in U.S. patent application Ser. No. 09/597,610, filed Jun. 20, 2000.

When the subject's measured aggregation statistic $\Theta_m$ (from equation 2.2 or 2.3) block 47 is less than the group threshold $\theta_g$-block 50, the test indicates the subject has ADHD. When the measured aggregation $\Theta_m$ statistic is greater than the predetermined threshold $\theta_g$, the test indicates the subject does not have ADHD-block 50 and no medication is required-block 51. The same threshold $\theta_g$ may be used for all subjects or $\theta_g$ may have a value that is different for different groups based on gender or age.

Determination of Proper Dosage

Figure 3B:
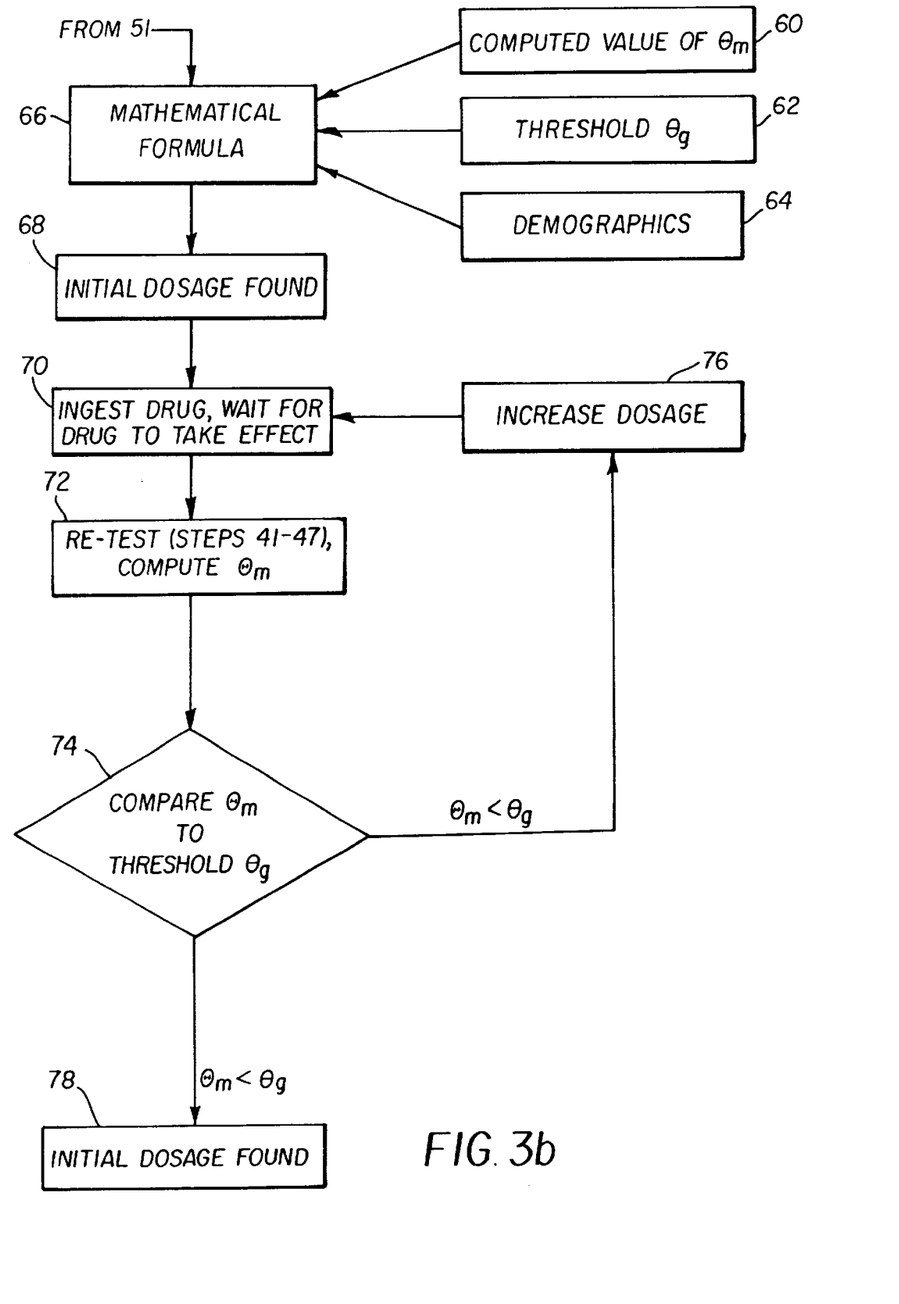

Now referring to FIG. 3b, based upon the computed value of the aggregation statistic $\Theta_m$-block 60 and the predetermined threshold value $\theta_g$-block 62, a mathematical formula-block 66 is used to compute the proper dosage-block 68 for subjects who are diagnosed as having ADHD. This mathematical formula may also include demographic information-block 64, including gender, age and weight. An example of such a mathematical formula is the following:

$$\text{Dosage} = 100 \times (\theta_{g-\Theta_m} - 1) + 100 \times \text{gender}$$

where the dosage is in milligrams of a drug, and where gender is coded as 0 if the patient is female and 1 if the patient is male. For example, if $\theta_g=10$ and $\Theta_m=8$, and the patient is male, the example formula would call for a dosage of $100 \times (10-8-1) + 100 \times 1 = 200$ milligrams of the drug.

Medication Effectiveness Indicator

If the prescribed medication is effective in correcting the ADHD, then the measured physiologic diagnostic indicator $\Theta_m$ (as defined by equation 2.2 or 2.3) would be expected to come within the normal range and exceed $\theta_g$ during the time the patient is medicated.

In studies using this method, subjects who had ADHD were tested while on medication and again while not on medication. The diagnostic indicator $\Theta_m$ was higher on average when the subject was medicated, and lower on average when the subject was not medicated. This is consistent with what the hypothesis would predict. Paired t-tests (for example, see Hildebrand, D. K. and Ott, L. (1991), *Statistical Thinking for Managers*, PWS-KENT Publishing, Boston, p. 440) showed this change in $\Theta_m$ was statistically significant ($\alpha=0.05$), indicating that the method described was able to determine changes brought about by the medication.

Figure 8:
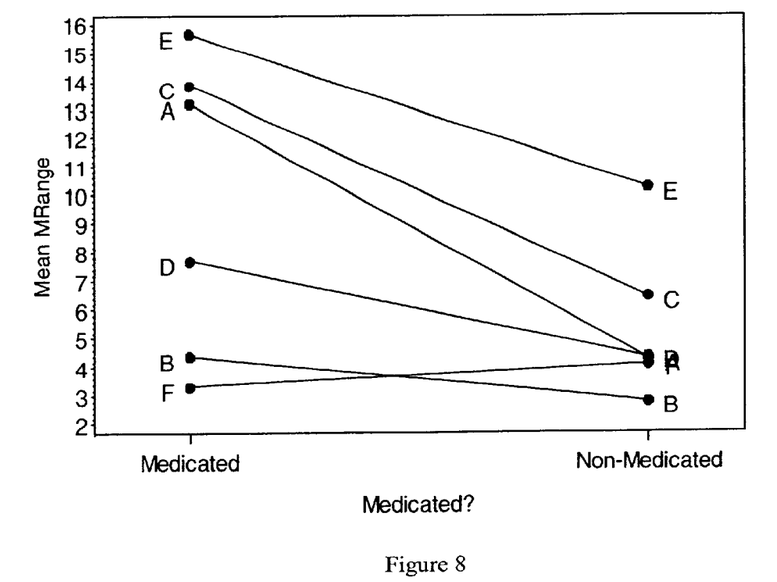
FIGS. 8, 9 and 10 are graphical illustrations respectively showing mean Mrange values and Mrange variance for both medicated and non-medicated sessions.

When we let $\Theta^m$ be the mean Mrange, FIG. 8 shows the values of $\Theta_m$ for both the medicated and non-medicated sessions. The lines connect the two data points from each subject, and a subject identifier is given by a letter next to the data point. When the lines slope downward, they indicate a decrease in $\Theta_m$ when the subject was not medicated, which is what the hypothesis predicts. We see that five of the six lines in FIG. 8 slope downward (subjects A, B, C, D, and E). We see that the sixth line (subject F) slopes upward but only by a small amount. The mean Mrange shows an average change between medicated and non-medicated sessions of 4.3, the standard deviation of this change is 3.6 and with six subjects, the paired t-test has a p value of 0.0337, indicating statistical significance with $\alpha=0.05$.

Figure 9:
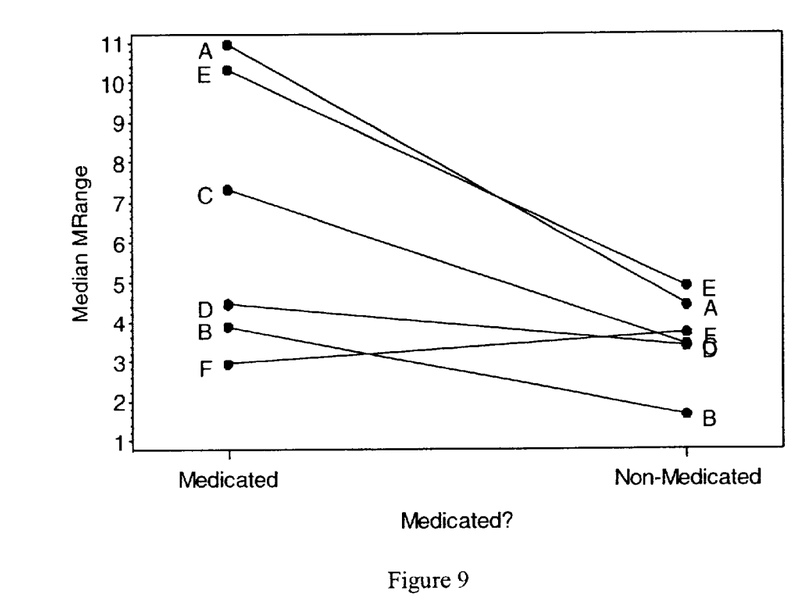

When $\Theta_m$ is the median Mrange, the results are shown in FIG. 9. Again, five of the six lines (subjects A, B, C, D and E) slope downward and one line (subject F) slopes upward. The mean of these changes between medicated and non-medicated sessions is 3.066, the standard deviation is 2.74 and with 6 subjects, the p value for the paired t-test is 0.0409, again indicating statistical significance with $\alpha=0.05$.

Figure 10:
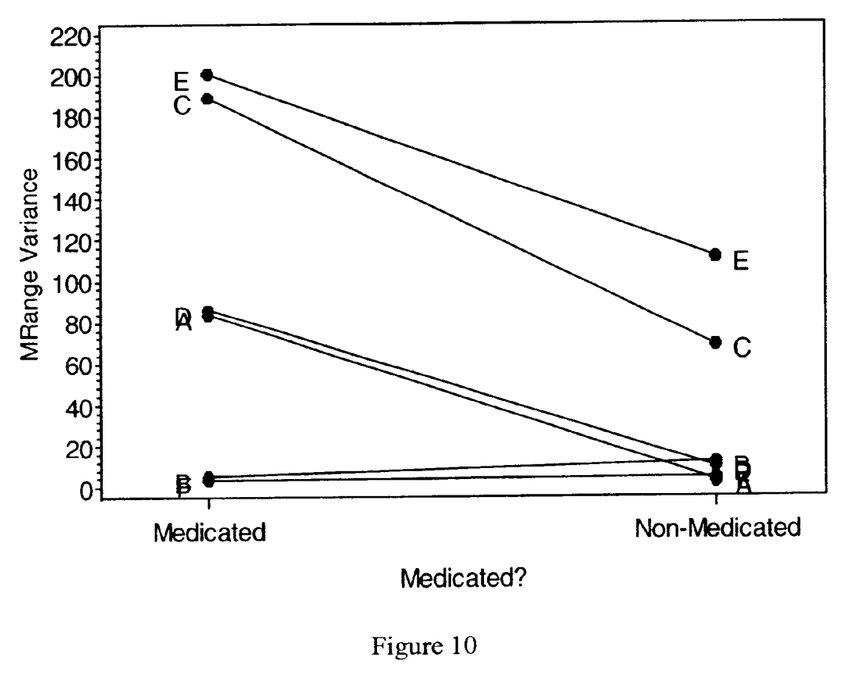

When $\Theta_m$ is the variance of the Mrange, the results are shown in FIG. 10. Again, four of the six lines (subjects A, C, D and E) slope downward by quite a large amount, and the other two lines (subject B and F) slope upward slightly. The mean of these changes between medicated and non-medicated sessions is 60.03, the standard deviation is 51.67 and with 6 subjects, the p value for the paired t-test is 0.0360, again indicating statistical significance with $\alpha=0.05$.

Thus, to determine if the dosage is effective, the patient will be re-tested according to the following procedure as illustrated in FIG. 3b. The subject will take the prescribed dosage of the medication and then wait a certain period of time-block 70. The subject's peripheral temperature will be measured and $\Theta_m$ will be calculated-block 72. This time period can range from the minimum time it takes for the drug to become effective after ingestion, to the maximum length of time the drug is effective after ingestion. Ideally, the test will occur at a time period equal to the drug's half-life in the body. Next, compare the newly computed $\Theta_m$ value to threshold $\theta_g$-block 74. If value of $\Theta_m$ moves to the non-ADHD region (above threshold $\theta_g$), it is concluded that the medication and dosage are appropriate-block 78. If value of $\Theta_m$ remains in the ADHD region (below threshold $\theta_g$), it is concluded that a larger dosage is needed block 76. The dosage can be increased according to best medical practices. This procedure blocks 70–78 can be repeated until appropriate medication and dosages are determined such that the patient's $\Theta_m$ value, when re-tested, is in the non-ADHD region (above threshold $\theta_g$).

Because a patient's physiology can change over time, the effective dosage may change over time as well. Thus, the patient needs to be monitored during the treatment period in accordance with the best medical practices. One such monitoring scheme, which should be followed during the entire time the patient is taking the drug, is to periodically re-test the patient. The interval between these periodic tests can for example, be one month to one year. The monitoring procedure involves repeating blocks 70–78. In one embodiment of the invention, the initial dosage found-block 78 could be replaced with an enhancement in which, if $\Theta_m$ exceeds $\theta_g$ by a large amount, the dosage is decreased, while if $\Theta_m$ exceeds $\theta_g$ by a small amount, then the proper dosage has been found.

The invention has been described in detail with particular reference to certain preferred embodiments thereof, but it will be understood that variations and modifications can be effected within the spirit and scope of the invention.

| PARTS LIST | |
|---|---|
| 10 | subject |
| 12 | chair |
| 13 | table |
| 14 | screen |
| 16 | fingertip |
| 17 | digit groove |
| 18 | analyzer module |
| 20 | earphones |
| 22 | sensor |
| 24 | on/off switch |
| 26 | display |
| 27 | cable |
| 28 | sensor module |
| 29 | cable |
| 30 | battery |
| 32 | external low voltage power supply port |
| 34 | groove |
| 36 | temperature sensor |
| 41 | temperature sampling circuit |
| 42 | data storage |
| 43 | window blocking |
| 44 | Fourier transform |
| 45 | Magnitude calculation |
| 46 | Mrange calculation |
| 47 | aggregation block |
| 48 | threshold comparison block |
| 49 | previously determined threshold $\theta_g$ block |
| 50 | decision block |

-continued

PARTS LIST

| 51 | no medication required block 51 |
| 60 | computed value of aggregation statistic $\Theta_m$ |
| 62 | threshold value $\theta_g$ |
| 64 | demographics |
| 66 | mathematical formula to determine initial dosage |
| 68 | initial Dosage |
| 70 | ingest drug and wait |
| 72 | re-test step |
| 74 | compare new $\Theta_m$ to threshold $\theta_g$ |
| 76 | increase dosage |
| 78 | proper dosage |

What is claimed is:

1. A method for determining the appropriate dosage of a medication to treat Attention Deficit Hyperactivity Disorder (ADHD) in an individual who has ADHD comprising:
    measuring the stress of a human subject by sampling the peripheral skin temperature of a human subject during a predetermined time interval when the subject is in an inactive state to provide sampled peripheral skin temperature data;
    analyzing the sampled peripheral skin temperature data for a pre-selected parameter to determine whether said pre-selected parameter has a value indicative of ADHD; and
    determining the proper dosage of a medication to treat ADHD based upon said determined value of said pre-selected parameter; and
    at a time subsequent to administering said dosage, determining if the administered dosage of medication is actually effective at removing the effects of ADHD as measured by said pre-selected parameter.

2. The method of claim 1 wherein said analyzing includes: dividing the sampled data into windows of subsets of data;
    processing the subset data for each window with a Fast Fourier Transform (FFT) algorithm to produce FFT data having magnitude values;
    calculating a magnitude range value for each window; and
    aggregating the magnitude range values to produce an aggregate value; and
    comparing the produced value with a previously determined threshold value to determine said proper dosage.

3. The method of claim 1 including an earphone worn by the subject during said predetermined time interval to block out ambient noise or to receive white noise to reduce or eliminate audio stimulus from the ambient environment during said time interval.

4. The method of claim 3 including a source of white noise coupled to said earphone to provide white noise during said predetermined time interval.

5. The method of claim 1 including glasses or goggles worn by the subject during said predetermined time interval to block out or eliminate ambient visual stimulus from the ambient environment during said time interval.

6. The method of claim 2 wherein demographic information including gender, age and weight of the human subject are used to be determined said proper dosage.

7. The method of claim 2 wherein said threshold value is chosen so that determined values above said threshold value indicate normalcy and determined values below said threshold value indicate ADHD and wherein said dosage is increased as a function of how great is the difference between said produced value and said threshold value.

8. The method of claim 1 including administering said determined dosage of said human subject;
    after waiting a period of time for the medication to take effect, repeating said sampling and analyzing to produce a new value of said pre-selected parameter, and based on said new value, (a) maintaining said dosage if said new value is indicative of ADHD, or (b) increasing said dosage if said new value is indicative of ADHD.

9. The method of claim 8 wherein said period of time is a function of the medication's half-life in said human subject's body.

10. The method of claim 2 including administering said dosage of said medication to said human subject, after waiting a period of time for the medication to take effect, repeating said dividing, processing, calculating and aggregating to produce a new aggregate value, and based on said new aggregate value, (a) maintaining said dosage if said new aggregate value when compared to said previously determined threshold value is not indicative of ADHD, or (b) increasing said dosage if said new aggregate value when compared to said previously determined threshold value is indicative of ADHD.

11. The method of claim 10 wherein said period of time is a function of the medication's half-life in said human subject's body.

12. The method of claim 1 further comprising the step of measuring stress using a technique selected from;
    bilateral temperature variability, heart rate variability, muscle tension, bilateral muscle tension imbalance, galvanic skin response eye saccades, blood oxygen, salivary IGA, electroencephalography peripheral blood flow and peripheral blood flow variability (PPG).

13. The method of claim 1 wherein in said testing the peripheral skin temperature of at least one hand of each individual is sampled.

14. The method of claim 1 wherein in said testing, the peripheral temperature of the dominant hand of each individual is tested.

15. The method of claim 13 wherein the peripheral skin temperature of both hands of each individual is sampled and said parameter value for that individual is produced by analyzing the sampled peripheral skin data from both said hands.

16. The method of claim 1 wherein said method uses one or more of the following for aggregation;
    including the standard deviation, range, interquartile distance, skewness, kurtosis, Winsorized means, Winsorized variance, robust estimates of mean, and robust estimates of variance.

17. The method of claim 2 wherein said process uses one or more of the following for aggregation;
    include using the data from only one hand—either the left hand, the right hand or the dominant hand.

18. The method of claim 1 wherein said pre-selected parameter is calculated from a Fourier Transform, of said skin temperature data.

19. The method of claim 1 wherein said pre-selected parameter is calculated from a Wavelet Transform of said skin temperature data.

* * * * *

UNITED STATES PATENT AND TRADEMARK OFFICE
CERTIFICATE OF CORRECTION

| | | |
|---|---|---|
| PATENT NO. | : 6,743,182 B2 | Page 1 of 1 |
| APPLICATION NO. | : 10/301401 | |
| DATED | : June 1, 2004 | |
| INVENTOR(S) | : Miller et al. | |

It is certified that error appears in the above-identified patent and that said Letters Patent is hereby corrected as shown below:

Column 5,
   Line 18ff., replace "$\Phi_1 (f_m)$ -Tan$^{-1}$ [B$(f_m)$/A$(f_m)$]" with
      --$\Phi_1 (f_m)$ =Tan$^{-1}$ [B$(f_m)$/A$(f_m)$]--; and

Line 22ff., replace "$M_1 (f_m) = \sqrt{B(f_m)^{2 + A(fm)2}}$" with
      --$M_1 (f_m) = \sqrt{B(f_m)^2 + A(f_m)^2}$ --.

Column 7,
   Line 15ff., replace "Dosage=100X($\theta_{g\text{-}\Theta m}$-1) +100Xgender" with
   --Dosage=100X($\theta_g$-$\Theta_m$-1) +100Xgender--; and
   Line 39, replace "$\Theta^m$" with --$\Theta_m$--.

Column 10,
   Line 30, Claim 12, replace "from;" with --from--;
   Line 33, Claim 12, replace "eye response" with --eye response; --;
   Line 34, Claim 12, replace "electroencephalography" with
      --electroencephalography, --;
   Line 35, Claim 12, replace "flow" with --flow, --; and
   Line 59, Claim 18, replace "Transform," with --Transform--.

Signed and Sealed this

Twenty-second Day of May, 2007

JON W. DUDAS
*Director of the United States Patent and Trademark Office*